United States Patent [19]
Okuyama et al.

[11] Patent Number: 5,364,520
[45] Date of Patent: Nov. 15, 1994

[54] CAPILLARY COLUMN PACKED WITH GLUCOMANNAN GEL FOR CAPILLARY ELECTROPHORESIS AND METHODS FOR MAKING AND USING SAME

[75] Inventors: Tsuneo Okuyama, Kanagawa; Tomonori Izumi; Masato Yamaguchi, both of Tokyo, all of Japan

[73] Assignee: Kurita Water Industries, Ltd., Tokyo, Japan

[21] Appl. No.: 987,758

[22] Filed: Dec. 10, 1992

[30] Foreign Application Priority Data

Dec. 10, 1991 [JP] Japan ................ 3-350146

[51] Int. Cl.$^5$ ................ C25B 9/00
[52] U.S. Cl. ................ 204/299 R; 204/182.8; 252/315.1; 252/315.3; 536/114
[58] Field of Search ........ 204/299 R, 182.8; 252/315.1, 315.3; 536/114

[56] References Cited

U.S. PATENT DOCUMENTS 4,882,426  11/1989  Motozato ................ 536/114
5,089,111  2/1992  Zhu et al. ................ 204/180.1

Primary Examiner—John Niebling
Assistant Examiner—C. Delacroix-Muirheid
Attorney, Agent, or Firm—Millen, White, Zelano & Branigan

[57] ABSTRACT

A packing material for capillary electrophoresis comprises capillary electrophoresis in an apparatus having a capillary column, by charging a sample into an end of the capillary column and discharging the sample from the other end of the capillary column, is conducted using a capillary column prepared by packing the column with a packing material comprising glucomannan and then forming a gel in situ from the packed glucomannan. The packing material is packed into the capillary easily and forms a homogeneous gel therein which shows no damage by formation of bubbles and the like and thus can be utilized with stability, has superior health safety and is excellent with respect to biodegradation.

11 Claims, No Drawings

CAPILLARY COLUMN PACKED WITH GLUCOMANNAN GEL FOR CAPILLARY ELECTROPHORESIS AND METHODS FOR MAKING AND USING SAME

BACKGROUND OF THE INVENTION

1. Field of the invention

The present invention relates to a novel capillary column for capillary electrophoresis. More particularly, it relates to a capillary column which employs a packing material for capillary electrophoresis which can be easily packed into a capillary, can form a homogeneous gel in the capillary, shows no damage on the formed gel by formation of bubbles and the like, thus, can be utilized with stability and is favorably utilized for separation and analysis of proteins, nucleic acids, amino acids and the like.

2. Description of the prior art

Electrophoresis has been utilized for the analysis of proteins, nucleic acids, decomposition products thereof and other like various substances. The electrophoresis comprises various methods, such as gel electrophoresis, filter paper electrophoresis, isoelectric point electrophoresis and the like. Because a gel generally prevents occurrence of convection and protects the sample from adverse effects of reactions such as generation of gas at the electrode, it is a favorable medium for fractionating proteins and nucleic acids and the like to narrow bands.

Capillary electrophoresis is a method of gel electrophoresis preformed in a gel packed in a capillary. As the gel for this method, polyacrylamide gel which does not show electroosmosis is generally utilized.

Recently, a method of utilizing agarose which is a natural polysaccharide as the gel for the capillary was proposed (Journal of Chromatography, Volume 458, Pages 303-312 (1988)). A method of utilizing Curdlan ® which is a β-glucan as a gel for the electrophoresis was also proposed (Analytical Sciences, Volume 7, Pages 811-812 (October 1991)).

However, polyacrylamide gel has problems: (1) bubbles tend to be formed by contraction of volume during the preparation of gel (polymerization) and unfavorable phenomena frequently take place, such as damage of the gel by the formation of bubbles during the preparation of the gel or during the operation of the electrophoresis; (2) the operation of packing the packing material into the capillary is complicated and requires skill; (3) because unstable crosslinking agents must be utilized, preparation of homogeneous gel is not easy and the operation must be completed in a short time; and (4) because acrylamide reportedly has an adverse effect on health, care must be taken to avoid an adverse effect on health.

The method of utilizing agarose as the gel for the capillary has the fatal problem that agarose is mechanically weak and flows out of the capillary during the electrophoresis. Furthermore, the gel formed by agarose becomes heated during the operation of the electrophoresis and the rise of temperature causes melting of the gel. This is another cause of the flowing out of the capillary. Thus, a sample mixture cannot be separated with good reproducibility by the electrophoresis utilizing the capillary column (namely gel-filled capillary) packed with agarose gel.

According to the published method of utilizing curdlan as the gel, a column of 3.5 nun diameter was used. The column of this size cannot be regarded as a capillary column. Also, the molecular weight of Curdlan ® is so low (at most 100,000) that it is required to pack Curdlan ® into a column at high concentration like 15 weight % as described in the above mentioned journal in order to use it as the separation column. It is very difficult to pack the material of such a high concentration into an ordinary capillary whose diameter is generally less than 1 mm. Furthermore, in a column of this concentration, high molecular weight components like proteins or nucleic acids cannot be separated even though low molecular weight components may be separated.

SUMMARY OF THE INVENTION

The present invention accordingly has an object to solve the problems of the conventional polyacrylamide gel described above and provide a capillary column which employs a packing material for the capillary electrophoresis which can be easily packed, can form a homogeneous gel in the capillary, shows no damage on the formed gel by formation of bubbles and the like, can be utilized with stability and has excellent safety with respect to health. The present invention has also an object of providing a method of producing the capillary columns and a method of their use in capillary electrophoresis apparatus.

Extensive investigations undertaken by the present inventors with the objects described above lead to a discovery that a packing material comprising glucomannan is effective for achieving the object. The present invention has been completed on the basis of the discovery.

The packing material employed in the capillary columns of this invention is a glucomannan.

The method of conducting a capillary electrophoresis using a capillary column of this invention comprises the steps of charging a sample into an end of the capillary column and discharging the sample from the other end of a capillary column prepared by packing the capillary with a solution or suspension glucomannan and then forming a gel from the packed glucomannan in situ in the column.

Other and further objects, features and advantages of the invention will appear more fully from the following description.

DESCRIPTION OF THE PREFERRED EMBODIMENTS

The invention is described in detail in the following.

The glucomannan utilized in the invention is a polysaccharide comprising mannose and glucose in about 2:1 mol ratio. The glucomannan can be obtained from various sources and the origin is not particularly limited, although a preferred source is mannan from konjak (devil's-tongue jelly). As the konjak mannan, a material prepared by dissolving into water a fine powder utilized as a material of a paste from the konjak followed by purification with an alcohol or the like, commercial materials such as Propol ® (a product of Shimizu Kagaku Co., Ltd.) and the like can be utilized.

The konjak mannan is the major component of the konjak. It is entirely free from toxicity, shows excellent health safety and has excellent biodegradability as well.

The glucomannan utilized in the invention preferably has a molecular weight in the range from 50,000 to 2,000,000, most preferably in the range from 100,000 to 2,000,000. Concentration of the gel and molecular weight of the packing material are suitably selected according to the molecular weight of the proteins, nucleic acids or the like materials to be separated. The mannan obtained from the natural konjak generally has a molecular weight in the range from 1,000,000 to 2,000,000. When a mannan having a lower molecular weight is needed, the mannan from the natural source can be treated for degradation by chemical hydrolysis or by degradation with an enzyme.

In the method of electrophoresis, higher gel concentrations are generally effective for separation of low molecular weight components. However, an excessively high gel concentration causes difficulty in packing the gel into the capillary. Lower gel concentrations are generally effective for separation of high molecular weight components. However, an excessively low gel concentration causes difficulty in the formation of gel. A glucomannan having a higher molecular weight forms gel at a lower concentration and, on the other hand, a glucomannan having a lower molecular weight requires a higher concentration.

Thus, it is preferable that the optimum concentration of gel is suitably selected according to the molecular weight of the glucomannan utilized and the molecular weight of the sample to be separated. When the molecular weight of the glucomannan is 100,000, 500,000 or 1,000,000, the concentration of the gel is selected in the range from 0.5 to 5 weight/volume %, in the range from 0.3 to 2 weight/volume and in the range from 0.1 to 1.5 weight/volume, respectively.

As the capillary column in which the packing material of the invention is packed, a capillary made of a glass, such as fused silica, or made of a synthetic resin, such as Teflon ®, having an inner diameter of 1 mm or less, preferably in the range from 10 to 500 $\mu$m and a length in the range from several centimeters to several meters is generally utilized.

A preferred example of the operation of a capillary electrophoresis utilizing the capillary column of the invention is described in the following. Glucomannan is added to a buffer solution such as trishydrochloric acid in an amount required for the desired concentration and dissolved or dispersed in it. The solution or the dispersion is packed into the capillary by an injection syringe or the like tool and then solidified. Thus, a gel comprising a network structure of glucomannan is formed in the capillary. When the buffer solution utilized for preparation of the glucomannan gel is different from the buffer solution in the sample, the glucomannan is sufficiently equilibrated with the buffer solution in the sample. A high voltage electricity source is connected to the two ends of the capillary and the electrophoresis is conducted according to the conventional method.

The molecular weight of the sample to be separated by this invention is preferably from several hundreds to several ten millions.

The invention will be understood more readily with reference to the following examples; however, these examples are intended to illustrate the invention and are not to be construed to limit the scope of the invention.

EXAMPLE 1

As the apparatus of capillary electrophoresis, CE-800 ® (a product of Nippon Bunko Kogyo Co., Ltd.) was used. A silica capillary having an inner diameter of 100 $\mu$m and a length of 50 cm was used as the capillary for separation and a commercial product, Propol ® (a product of Shimizu Kagaku Co., Ltd., the average molecular weight of 1,360,000) was used as the glucomannan.

A buffer solution of 0.07M trishydrochloric acid-boric acid containing 0.014M of EDTA (pH 8.2) was prepared. The glucomannan was dissolved in the buffer solution to form a 0.25 weight % solution of the glucomannan. The solution was heated for 10 minutes at 100° C. and then packed into the silica capillary with a plastic syringe. Glucomannan gel was formed by standing for 40 minutes at the room temperature.

A DNA sample ($\phi \times 174$ HaeIII digest, a product of Nippon Gene Co., 0.38 mg/ml) was introduced into the capillary column for 21 seconds under the voltage of 5 kV from the cathode side by the method of electrophoresis without preliminary treatment such as treatment by a modifier or by heating. The electrophoresis was performed at a constant voltage of 5 kV and the detection was made by the ultraviolet ray of the wave length of 260 nm with an ultraviolet detector placed at the position separated from the cathode end of the capillary by 20 cm. The result was obtained in the third run of the electrophoresis.

The DNA sample was separated to 12 peaks including shoulder peaks after 40 minutes of the electrophoresis. This result was similar to that obtained by electrophoresis with 5 weight % polyacrylamide slab gel, which is shown as a band spectrum in the upper part of the figure. Among the 12 peaks, the peak at 7 minutes is considered to correspond to an impurity and the remaining 11 peaks during 17 to 35 minutes are considered to correspond to the fragment components of 72, 118, 194, 234, 271, 281, 310, 603, 872, 1078 and 2353 bp, respectively.

The result of the eleventh run showed a similar separation of the components. Thus, it is shown that the packing material of the invention can be utilized with excellent stability.

While the invention has been particularly shown and described with reference to preferred embodiments thereof, it will be understood by those skilled in the art that the foregoing and other changes in form and details can be made therein without departing from the spirit and scope of the invention.

To summarize the advantages obtained by the invention: (1) packing the capillary is easy and the required time for the packing can be reduced in comparison with conventional agents; (2) no damage by formation of bubbles and the like is exhibited in the formed gel and, thus, the capillary column has excellent stability; (3) a gel is formed homogeneously in the capillary; (4) the agent used to form the gel has no toxicity at all and its use has excellent safety with respect to health; and (5) the agent used to form the gel causes no environmental contamination because it is biodegradable. The packing material is favorably utilized for separation and analysis of proteins, nucleic acids, amino acids and the like.

What is claimed is:

1. In a gel-packed capillary column adapted for capillary electrophoresis, the improvement wherein the column is packed with a glucomannan gel.

2. A packed capillary column for capillary electrophoresis as claimed in claim 1 wherein the glucomannan is obtained from konjak.

3. A packed capillary column for capillary electrophoresis as claimed in claim 1 wherein the glucomannan has a molecular weight in the range from 50,000 to 2,000,000.

4. In a method of conducting a capillary electrophoresis in a capillary column connected to a source of high voltage and which comprises the steps of charging a sample into an end of the capillary column and discharging the sample from the other end of the capillary column, the improvement wherein the capillary column is a gel-packed column according to claim 1.

5. A method according to claim 4, wherein the gel-packed column is produced by adding an ungelled but gellable buffer solution or dispersion of the glucomannan to the capillary and permitting the solution or dispersion to gel therein.

6. A packed capillary column according to claim 1, wherein the glucomannan has a molecular weight in the range from 1,000,000 to 2,000,000.

7. A packed capillary column according to claim 1, wherein the glucomannan present therein is obtained from a natural source thereof by chemical hydrolysis or enzymatic degradation.

8. A packed capillary column according to claim 1, wherein the glucomannan has a molecular weight in the range of 100,000, 500,000 or 1,000,000 and the concentration of the glucomannan in the gel is in the range of 0.5 to 5 wt/vol %, 0.3 to 2 wt/vol % or 0.1 to 1.5 wt/vol %, respectively.

9. A method of producing a gel-packed capillary column according to claim 1, which comprises the steps of packing the column with a solution or dispersion of glucomannan in a buffer at a concentration suitable for gel electrophoresis and converting the solution or dispersion into a gel in situ in the capillary column.

10. A method of producing the gel-packed capillary column of claim 1, which comprises dissolving the glucomannan in a buffer solution, heating the resultant solution, packing the heated solution in the capillary column and maintaining the packed capillary column at room temperature such that the solution gels.

11. In a gel-packed capillary column adapted for capillary electrophoresis, the improvement wherein the column is packed with a gel of glucomannan obtained from a natural source thereof by chemical hydrolysis or enzymatic degradation and has a molecular weight of 100,000, 500,000 or 1,000,000 and the concentration of the glucomannan in the gel is in the range of 0.5 to 5 wt/vol %, 0.3 to 2 wt/vol % or 0.1 to 1.5 wt/vol %, respectively.

* * * * *